United States Patent
Ulman (10) Patent No.: US 9,582,873 B2
(45) Date of Patent: *Feb. 28, 2017

(54) ACTIVE IMAGING SYSTEMS FOR PLANT GROWTH MONITORING

(71) Applicant: Trimble Navigation Limited, Sunnyvale, CA (US)

(72) Inventor: Morrison Ulman, Los Altos, CA (US)

(73) Assignee: Trimble Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/090,496

(22) Filed: Apr. 4, 2016

(65) Prior Publication Data

US 2016/0217562 A1    Jul. 28, 2016

Related U.S. Application Data (63) Continuation of application No. 14/319,075, filed on Jun. 30, 2014, now Pat. No. 9,336,584.

(51) Int. Cl.

| | |
|---|---|
| *G06T 7/00* | (2006.01) |
| *G06K 9/00* | (2006.01) |
| *H04N 5/225* | (2006.01) |
| *H04N 5/335* | (2011.01) |
| *H04N 5/33* | (2006.01) |
| *G06K 9/20* | (2006.01) |
| *B64C 39/02* | (2006.01) |
| *G01N 21/55* | (2014.01) |
| *G01N 21/84* | (2006.01) |

(52) U.S. Cl.
CPC .......... *G06T 7/0004* (2013.01); *B64C 39/024* (2013.01); *G01N 21/55* (2013.01); *G01N 21/84* (2013.01); *G06K 9/00657* (2013.01); *G06K 9/00771* (2013.01); *G06K 9/2036* (2013.01); *G06T 7/0002* (2013.01); *G06T 7/0012* (2013.01); *H04N 5/2256* (2013.01); *H04N 5/2258* (2013.01); *H04N 5/33* (2013.01); *H04N 5/332* (2013.01); *H04N 5/335* (2013.01); *B64C 2201/127* (2013.01); *G01N 2021/8466* (2013.01); *G06T 2200/04* (2013.01); *G06T 2207/10024* (2013.01); *G06T 2207/10048* (2013.01); *G06T 2207/30188* (2013.01)

(58) Field of Classification Search
CPC ...................................................... G01N 21/55
USPC ........................................ 348/207.1; 702/19
See application file for complete search history.

(56) References Cited

U.S. PATENT DOCUMENTS

| | | | |
|---|---|---|---|
| 8,731,836 | B2 | 5/2014 | Lindores et al. |
| 2010/0324830 | A1 | 12/2010 | Solie et al. |
| 2013/0217439 | A1 | 8/2013 | Ulman et al. |

OTHER PUBLICATIONS

Sergi Foix et al., "Lock-in Time-of-Flight (ToF) Cameras: A Survey", IEEE Sensors Journal, v. 11, p. 1-11, Mar. 2011.
Infineon, "Product Brief: Infineon 3D Image Sensor IRS10x0C", May 2013.
Softkinetic, "DS325 Close Interaction Time-of-Flight 3D Depth-Sensing Camera", 2013.
Texas Instruments, "QVGA 3D Time-of-Flight Sensor OPT8140", Oct. 2013.

*Primary Examiner* — Antoinette Spinks
(74) *Attorney, Agent, or Firm* — Kilpatrick Townsend & Stockton LLP (57) ABSTRACT

Active imaging systems for plant growth monitoring acquire images in which each pixel represents an absolute NDVI value obtained with active illumination.

18 Claims, 7 Drawing Sheets

ACTIVE IMAGING SYSTEMS FOR PLANT GROWTH MONITORING

RELATED APPLICATIONS

This application is a continuation of U.S. Ser. No. 14/319,075 filed on Jun. 30, 2014.

TECHNICAL FIELD

The disclosure is related to agricultural imaging systems.

BACKGROUND

Modern precision farming allows farmers to work more efficiently than ever before and spend less money on fertilizers and pesticides. Consumers enjoy lower prices for high quality produce, and farm chemical waste and runoff are reduced. Precision farming encompasses wide-ranging technologies including vehicle control, data management, materials handling and materials application, and environmental sensing. Falling within the broad category of environmental sensing are techniques for monitoring plant growth that help farmers detect problem areas in a field and develop nutrient prescription maps.

Plant growth may be estimated via measurements of normalized difference vegetative index or NDVI. NDVI is derived from optical reflectivity measurements of plants at different wavelengths:

$$NDVI = \frac{r_{NIR} - r_{VIS}}{r_{NIR} + r_{VIS}}$$

Here, $r_{NIR}$ and $r_{VIS}$ are reflectivity measured at infrared and visible wavelengths, respectively. 780 nm and 660 nm are commonly used NIR and VIS wavelengths, but other wavelengths may be used and other vegetative indices may be defined.

Reflectivity measurements $r_{NIR}$ and $r_{VIS}$ depend on estimating the ratio of reflected and incident light at particular wavelengths. Reflectivity used in computing NDVI may be based on illumination from the sun or illumination from a controlled light source such as a light emitting diode. Sunlight is a convenient, but not consistent, light source. The spectrum of sunlight at the surface of the earth varies with time of day and weather, for instance. NDVI obtained with sunlight illumination may be adequate for relative plant growth assessment, but determining absolute NDVI with sunlight illumination is problematic. Accurate nutrient prescription programs based on NDVI data usually require absolute NDVI measurements.

What are needed are imaging systems and methods for obtaining absolute NDVI data.

DETAILED DESCRIPTION

NDVI may be used as an input for algorithms to estimate crop yield potential and crop response to additional nitrogen fertilizer if the NDVI values are accurate. Generally, this means that the NDVI measurements are based on reflectivity data obtained under active illumination.

Active imaging systems for plant growth monitoring obtain NDVI images using active illumination rather than sunlight. Each pixel in an NDVI image represents an NDVI value that (along with other data) may be used to generate a fertilizer prescription.

The spatial resolution of typical nutrient prescription maps for broadacre crops is often tens of square meters. This is sufficient if growing conditions vary only gradually over that scale. For row crops or permanent crops, however, it may be useful to customize fertilizer treatment on a plant-by-plant basis. Obtaining NDVI estimates for each plant is tedious if only conventional, single-point NDVI measuring equipment is available. Active imaging systems for plant growth monitoring based on nascent lock-in pixel technology, on the other hand, may obtain 10,000 or more data points (i.e. from 10,000 or more pixels) simultaneously. Future imagers will be able to obtain millions of data points at once. As discussed further below, active imaging systems may be mounted on a variety of vehicular or airborne platforms potentially enabling rapid acquisition of high-spatial-resolution NDVI data.

Wherever the term "NDVI" is used herein, it is as an illustrative example of a vegetative index. The discussion is understood to include the possibility of other vegetative indices, such as enhanced vegetative index (EVI), that are based on optical reflectivity measurements at two or more wavelengths.

Figure 1A:
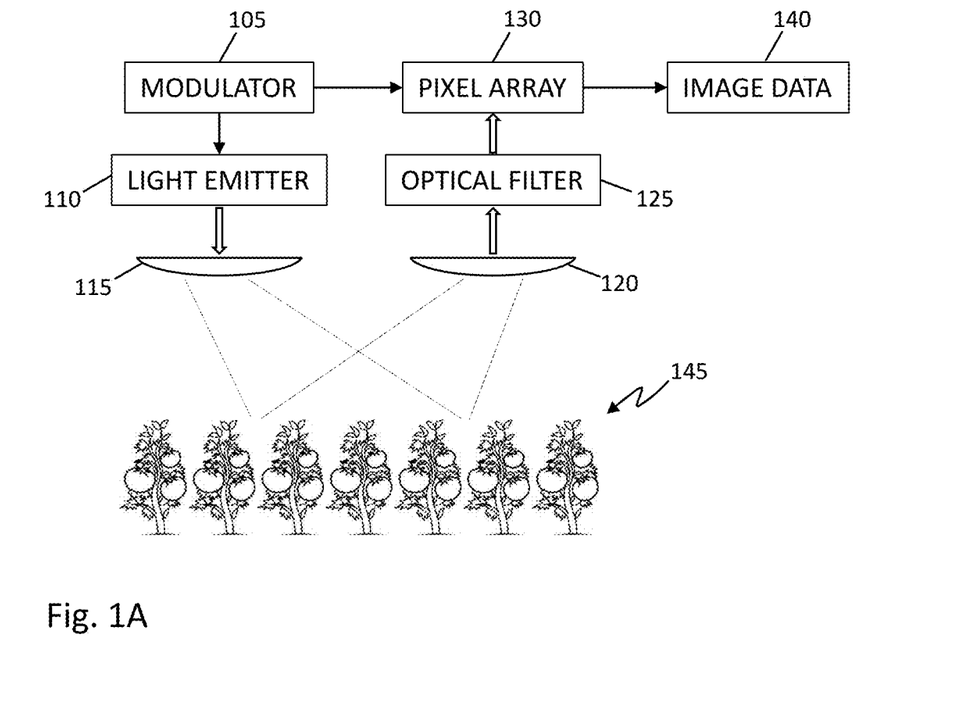
FIG. 1A is a block diagram of an active imaging system for plant growth monitoring.

FIG. 1A is a block diagram of an active imaging system for plant growth monitoring. In FIG. 1A modulator 105 sends a modulation signal to light emitter 110 and to pixel array 130. Light from light emitter 110 is projected by lens 115 onto crops 145. Light reflected by the crops is collected by lens 120, filtered by filter 125 and detected by pixel array 130. The output of pixel array 130 is image data 140 representing optical reflectivity values that are used to compute NDVI.

Pixel array 130 is an array of sensor pixels that use the modulation signal from modulator 105 to detect light emitted by light emitter 110 after the light is reflected from crops. The modulation signal is applied to each pixel in array 130, and demodulation permits detection of reflected light from crops (despite the presence of strong background light, such as sunlight) and thereby a reflectivity measurement of the crop. Optical detector arrays that have pixel-by-pixel demodulation capability have recently been developed for time-of-flight depth sensing purposes. These detector arrays are sometimes referred to as "lock-in, time-of-flight" sensor arrays or are said to have "lock-in" pixels. Foix et al. provide a review of such sensor arrays in "Lock-in Time-of-Flight (ToF) Cameras: A Survey", IEEE Sensors Journal, vol. 11, p. 1-11, March 2011, incorporated herein by reference.

Figure 1B:
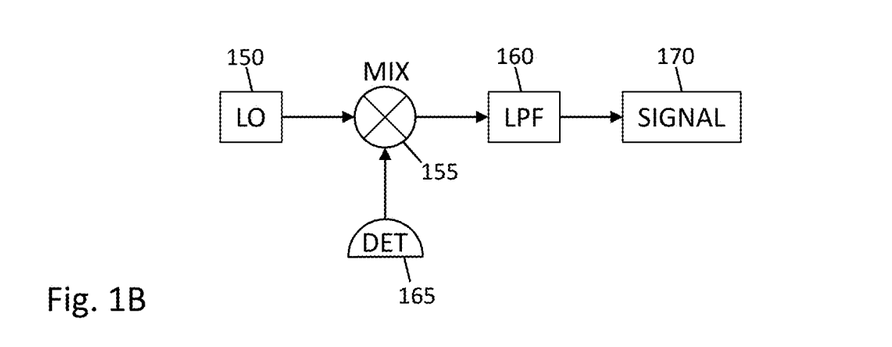
FIG. 1B is a block diagram of an example signal detection scheme.

FIG. 1B is a block diagram of an example signal detection scheme. Each pixel of an optical sensor pixel array such as 130 demodulates a detected light signal in a manner analogous to the scheme of FIG. 1B. In FIG. 1B, signals from local oscillator 150 and detector 165 are mixed in mixer 155. The output of the mixer is then passed through low-pass filter 160 to generate output signal 170. If a signal detected by the detector is represented as, $$V_D \sin(\omega_D t + \theta_D)$$

and the local oscillator signal is represented as, $$V_{LO} \sin(\omega_{LO} t + \theta_{LO})$$

then, with $\omega_D = \omega_{LO}$ and AC signal components removed by low pass filtering, the output signal 170 may be written, $$V_{OUT} = \frac{1}{2} V_D V_{LO} \cos(\theta_D - \theta_{LO}).$$

Here, V, $\omega$, and $\theta$ are the amplitude, frequency and phase of the respective signals. $V_{OUT}$, as written above, is the in-phase component of the output. The phase dependence of $V_{OUT}$ can be eliminated by detecting a quadrature component (e.g. with an LO phase shifted by $\pi/2$) and computing the square root of the sum of the squares of the in-phase and quadrature components. The result is the phase-independent magnitude of the detected signal, $V_D$. Similar analysis may be applied for square wave modulation when considered as a superposition of sine wave components.

A detection scheme such as the heterodyne example of FIG. 1B, or analogous digital techniques, may be used to obtain optical crop reflectivity data. The signal from local oscillator 150 is used to modulate a light source that illuminates the crop. Detector 165 detects light reflected from the crop. Background light is suppressed because the bandwidth of lock-in detection can be made very narrow. Only light modulated near the local oscillator frequency contributes to the output signal.

Pixel array 130 demodulates light on a pixel-by-pixel basis. "Lock-in, time-of-flight" sensor pixel arrays provide in-phase and quadrature outputs. Therefore modulator 105 may send a sine (or square) wave modulation signal to light emitter 110 or use a more complex modulation scheme involving a pseudo random noise code, binary phase shift keying, etc. Examples of commercially available lock-in pixel arrays include the IRS10x0C from Infineon and the OPT8140 QVGA 3D Time-of-Flight sensor from Texas Instruments. Pixel array 130 and modulator 105 may be implemented on one integrated circuit chip or as separate components.

Pixel array 130 generates data at a high rate. In-phase (I) and quadrature (Q) signals are converted to signal magnitude representing reflectivity, and reflectivity measurements at different wavelengths are inputs for NDVI calculations. Data manipulation from I and Q to reflectivity to NDVI may be performed directly on the sensor array chip, an ASIC (application specific integrated circuit), an FPGA (field programmable gate array), a general purpose microprocessor, or a combination of these. Thus, a "processor" that computes a vegetative index for each pixel in an array of sensor pixels may be logic included in the array itself or it may be an external ASIC, FPGA, or microprocessor.

Light emitter 110 may be based on light emitting diodes or diode lasers. Because NDVI is computed from reflectivity measurements at more than one optical wavelength, the light emitter is capable of emitting light at two or more wavelengths and includes emitters for each wavelength of interest. The light emitter receives a modulation signal from modulator 105 and emits light modulated by the modulation signal. A typical set up includes two light emitting diodes, or two diode lasers, one each centered at 660 nm and 780 nm. Light emitters for various wavelengths may be operated simultaneously or sequentially. Lenses 115 and 120 may be spherical or anamorphic. Anamorphic lenses are useful when a high-aspect-ratio detection area is imaged onto a rectangular detector array. For example a detection area having an aspect ratio of, for example, 10:1 may be imaged onto a 320×240 QVGA sensor pixel array using anamorphic lenses.

Optical filter 125 includes filters for each wavelength of interest. The filters may be used simultaneously or sequentially. Filters may be colored glass filters or optical interference filters, as examples. Although ideal filter characteristics are narrow-band and bandpass at the wavelength of interest, more limited filters such as high-pass or low-pass filters may be adequate in some situations. It is even possible to omit optical filters if unwanted background light is not too bright.

Figure 2:
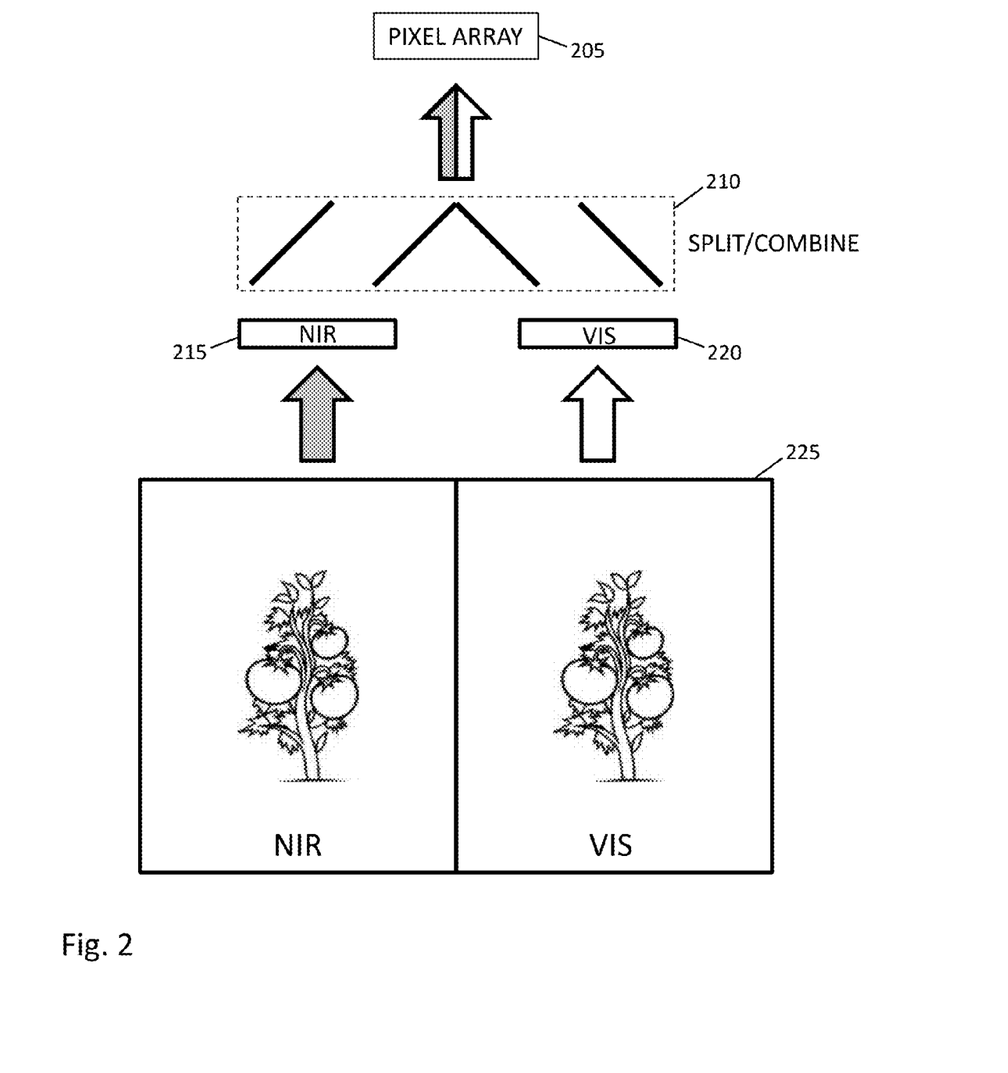
FIG. 2 illustrates a split imaging system for simultaneous two-wavelength image capture.

FIG. 2 illustrates a split imaging system for simultaneous two-wavelength image capture. In FIG. 2, pixel array 205 demodulates light on a pixel-by-pixel basis like pixel array 130 in FIG. 1. Splitter/combiner 210 and filters 215 and 220 cause two images of one scene—at two different wavelengths—to appear side-by-side on array 205.

Filters 215 and 220 are preferably band-pass filters for wavelengths of interest. For example, filter 215 may be centered at a near-infrared wavelength such as 780 nm while filter 220 may be centered at a visible wavelength such as 660 nm. Alternatively, filters 215 and 220 may be a low-pass and high-pass filter respectively.

Splitter/combiner 210 comprises mirrors such that a scene of, e.g. a single plant, appears as a two, side-by-side images 225 of the same plant, one each at wavelength selected by filters 215 and 220. (A similar splitter/combiner was described in "Cell phone NDVI sensor", U.S. Ser. No. 13/749,587, filed on Jan. 24, 2013 and incorporated herein by reference.) The two images, representing reflectivity at different wavelengths, may be combined to form an NDVI image; i.e. NDVI computed at each pixel.

Figure 3A:
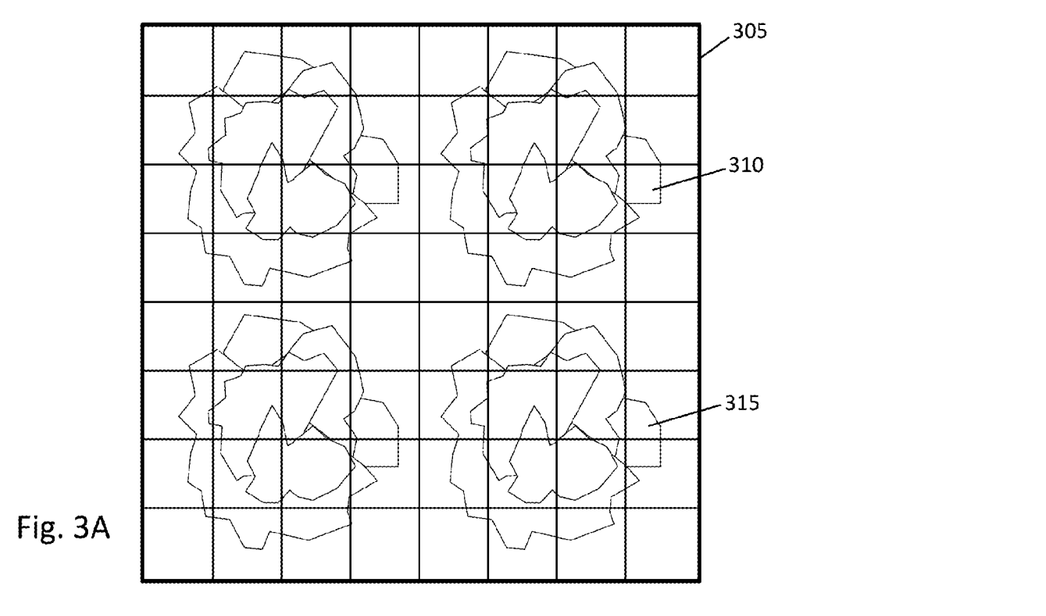
FIGS. 3A and 3B illustrate NDVI array data obtained at high magnification.
Figure 3B:
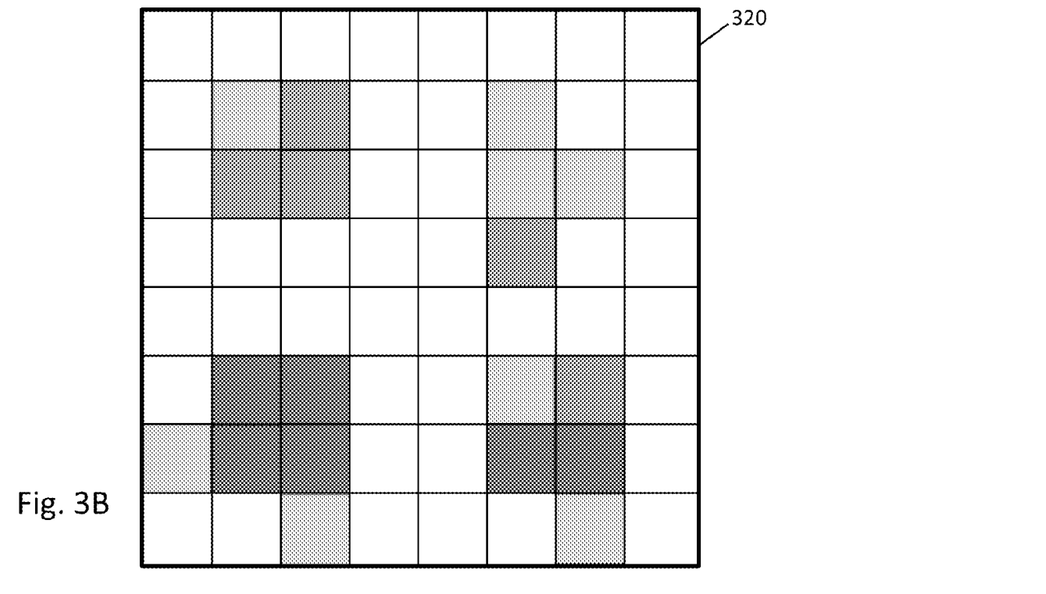
Figure 4A:
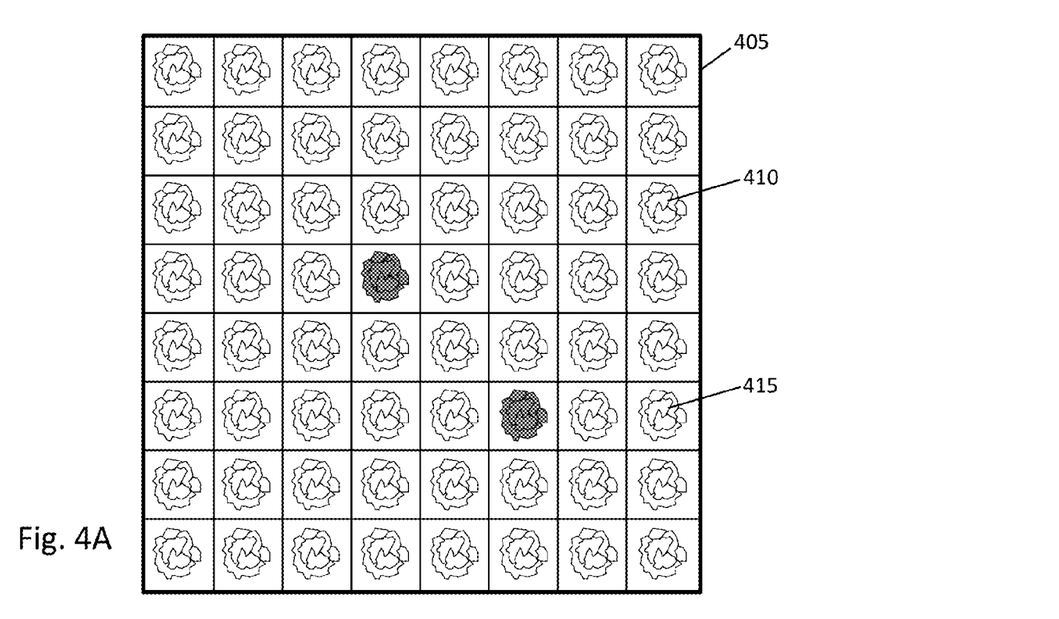
FIGS. 4A and 4B illustrate NDVI array data obtained at medium magnification.
Figure 4B:
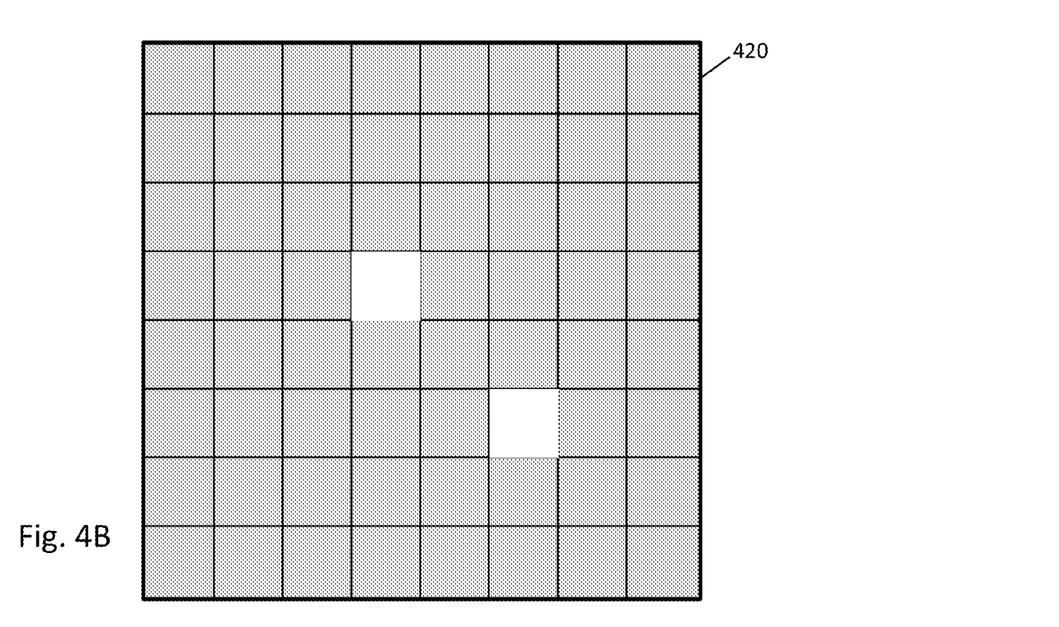
Figure 5A:
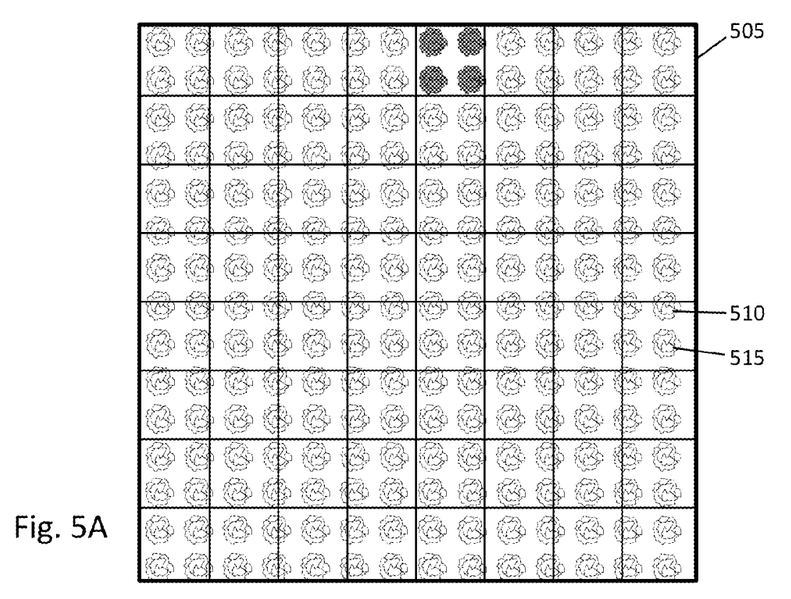
FIGS. 5A and 5B illustrate NDVI array data obtained at low magnification.
Figure 5B:
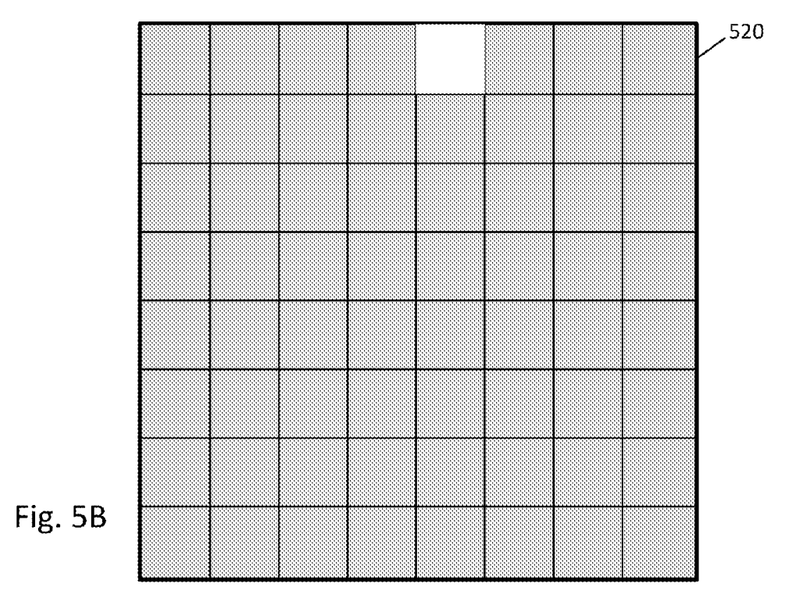

An active imaging system for plant growth monitoring may be operated at different magnifications as determined, for example, by lens 120 in FIG. 1. Lens 120 images an area of crops onto pixel array 130. Each pixel of the array sensor may detect light reflected by a single plant. Alternatively, each pixel may detect light from several plants, or light from each plant may be detected by several pixels. FIGS. 3, 4 and 5 illustrate these possibilities. FIGS. 3A, 4A and 5A show infinite-resolution images superimposed on an array of pixels. FIGS. 3B, 4B and 5B show corresponding array resolution array output, represented by grayscale shading at each pixel. FIG. 3, FIG. 4, and FIG. 5 illustrate NDVI array data obtained at high, medium and low magnification, respectively.

In FIG. 3A, 16×16 pixel array 305 is shown with an image of four plants (e.g. 310, 315) superimposed on it. Current state-of-the-art lock-in pixel arrays are available in sizes as large as QVGA (320×240) with larger arrays under development. In FIG. 3A light from each plant is detected by several pixels. (Said another way, each pixel receives light from less than one plant.) FIG. 3B shows an array of NDVI values based on output from array 305. In the figure, different shades of gray represent different NDVI levels.

FIGS. 4A and 5A show pixel arrays 405 and 505 respectively with images of plants (e.g. 410, 415 and 510, 515, respectively) superimposed on them. In FIG. 4A each pixel of the array sensor detects light from one plant—there is a one-to-one correspondence between plants and pixels. In FIG. 5A each pixel detects light from more than one plant. FIGS. 4B and 5B show arrays of NDVI values based on output from arrays 405 and 505, respectively. In the figures, different shades of gray represent different NDVI levels. In particular, some plants in FIGS. 4A and 5A are shaded dark to indicated poor health. Pixels corresponding to these plants show different NDVI values in FIGS. 4B and 5B.

Modern image geo-referencing capabilities, along with precision crop planting, enable precise registration between image pixels and individual plants. Active imaging systems for plant growth monitoring may thereby obtain NDVI data on a plant-by-plant basis for thousands of plants at a time when operated at one-to-one plant-to-pixel magnification as shown in FIG. 4. High magnifications (e.g. FIG. 3) may be used for averaging plant data over several pixels or identifying plants in contrast to surrounding dirt. A processor may average NDVI obtained over several pixels or it may average reflectivity measurements and compute NDVI for a group of pixels. Low magnifications (e.g. FIG. 5) may be used when growing conditions and/or plant health vary appreciably only over several inter-plant distances.

Figure 6:
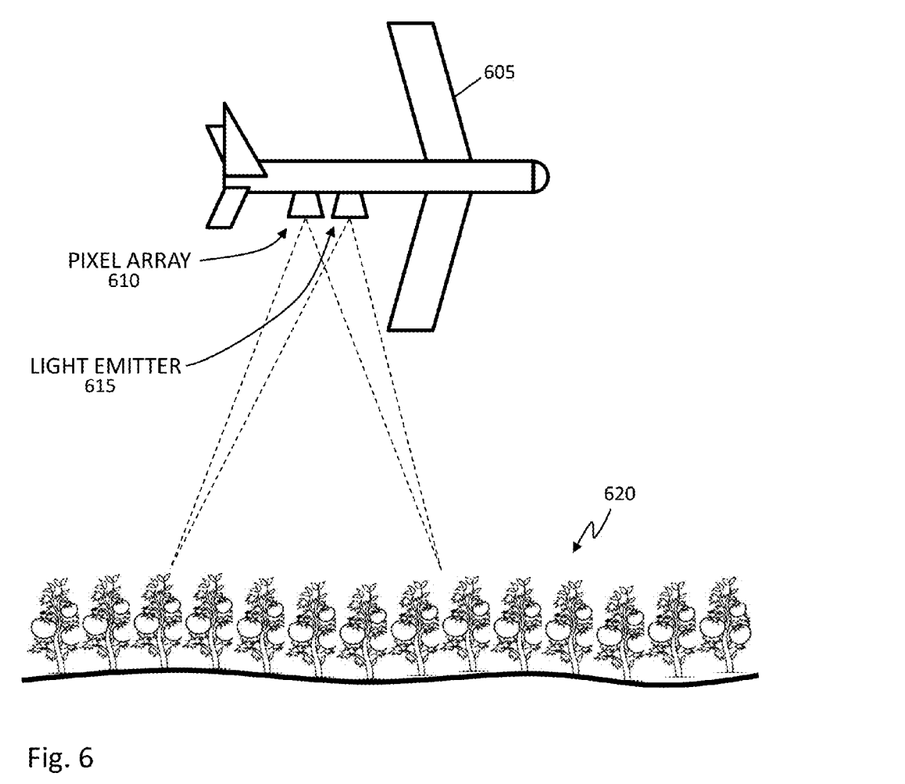
FIG. 6 illustrates an airborne active imaging system for plant growth monitoring.

Active imaging systems for plant growth monitoring may be operated from any structure or vehicle that has an adequate view of crops to be measured. All of the components of FIG. 1A may be included in a small, even handheld, package. An imaging system may be mounted on a farm vehicle, such as a self-propelled sprayer, and connected to a variable-rate fertilizer application system. For large area coverage, however, mounting an active imaging system on an airborne platform is provides an opportunity to cover ground quickly. Such platforms include conventional light airplanes and helicopters, and unmanned systems (e.g. unmanned airborne systems (UAS), unmanned aerial vehicles (UAV)). FIG. 6 illustrates an airborne active imaging system for plant growth monitoring.

In FIG. 6, aircraft 605 may be a light aircraft or UAV. Fixed- or rotary-wing aircraft are both viable alternatives. The aircraft carries all the components of the system of FIG. 1A, including a light emitter 615 capable of operating at two or more wavelengths and a lock-in pixel array 610. The aircraft may process and accumulate NDVI data with onboard processing and data storage (e.g. microprocessor and solid-state memory) and/or it may send data to a ground station via a radio link. An airborne active imaging system may cover hundreds or thousands of acres of crops per day and it may be operated day or night.

The airborne active imaging system of FIG. 6 may include a split imaging system for simultaneous two-wavelength image capture as shown in FIG. 2. Alternatively, the airborne system may employ a time-division-multiplexing scheme for obtaining plant reflectivity data as illustrated in FIG. 7.

Figure 7:
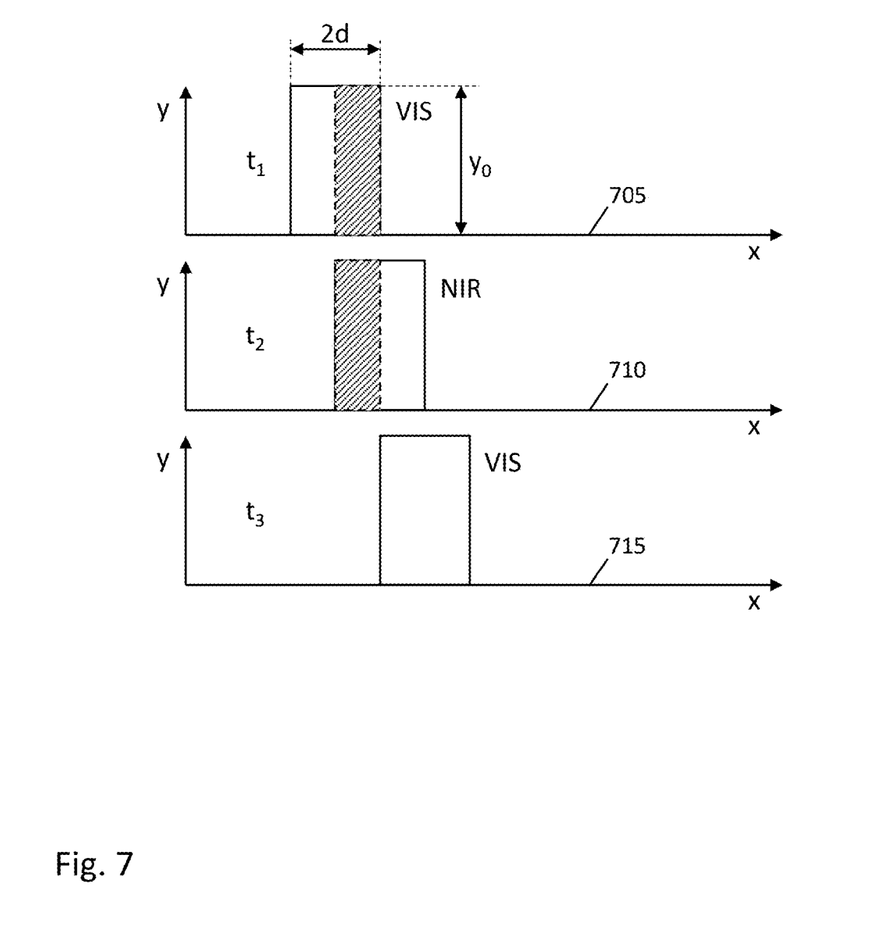
FIG. 7 illustrates a time-division-multiplexing scheme for obtaining plant reflectivity data.

FIG. 7 shows a plot of an area of land that is imaged with an active imaging system for plant growth monitoring at three successive times labeled $t_1$, $t_2$ and $t_3$. (Plot 705 illustrates an imaging area at $t_1$; plots 710 and 715 illustrate the same area at $t_2$ and $t_3$, respectively.) The imaging system obtains visible wavelength reflectivity data from a rectangular area having length (x-axis dimension) 2d and width (y-axis dimension) $y_0$ as shown in FIG. 7. (The aspect ratio of the desired imaging area may be matched to the sensor pixel array aspect ratio using anamorphic lenses.) The imaging system obtains a visible reflectivity image at time $t_1$. From time $t_1$ to time $t_2$, the imaging system moves a distance d in the x direction, and at $t_2$ the system obtains infrared wavelength reflectivity data from the 2d by $y_0$ area shown in plot 710. The d by $y_0$ hatched area in plots 705 and 710 represents the same piece of land: visible reflectivity data is obtained from it at time $t_1$, while infrared reflectivity data is obtained from it at time $t_2$. The 2d by $y_0$ field of view of the imaging system moves another distance d in the x-direction by time $t_3$ as shown in plot 715. Alternating visible and infrared measurements every time the imaging system moves by half the length of the imaged area (i.e. by d in this illustration) provides a way to obtain visible and infrared reflectivity from all areas of a field. This data acquisition scheme may be called time-division-multiplexing of reflectivity data.

When an active imaging system is operated in time-division-multiplexed mode, optical filters such as filters 125 in FIG. 1A may be moved in and out of the optical path to the sensor pixel array (e.g. 130 in FIG. 1A) such that the appropriate wavelength filter is in place at the right time. In the example of FIG. 7, for instance, a visible filter would be used at times $t_1$ and $t_3$, while an infrared filter would be used at time $t_2$.

Alternatively, when background light levels are low, such as at night, the system may be operated without optical filters. When wavelength selective filters are not used, it may also be possible to measure visible and infrared reflectivity simultaneously if the two wavelengths are modulated at different frequencies or with orthogonal signals. For example, if visible light (emitted by, e.g. emitter 110 in FIG. 1A) is modulated at 37 kHz and infrared light (also emitted by, e.g. emitter 110 in FIG. 1A) is modulated at 43 kHz, reflectivity from each wavelength may be obtained by using its local oscillator frequency in a lock-in pixel in the detection scheme of FIG. 1B. Alternatively, two emitted wavelengths may be modulated with orthogonal pseudo random noise codes.

As described above, an active imaging system obtains reflectivity measurements at two or more wavelengths as inputs for NDVI computation. Reflected light may be separated by modulation (e.g. frequency, phase, or pseudo random noise code), optical wavelength filters, time-division multiplexing, spatial splitter/combiners (e.g. splitter/combiner 210 in FIG. 2) or a combination of these.

Active imaging systems for plant growth monitoring acquire images in which each pixel represents an absolute NDVI value obtained with active illumination. Such systems may be used to obtain high-spatial-resolution NDVI data over wide areas, especially when mounted on an airborne platform such as an unmanned aerial vehicle. The NDVI data may then serve as input for prescription algorithms for additional crop nitrogen. High spatial resolution enables plant health monitoring and nutrient assistance on a plant-by-plant basis.

The above description of the disclosed embodiments is provided to enable any person skilled in the art to make or use the invention. Various modifications to these embodiments will be readily apparent to those skilled in the art, and the principles defined herein may be applied to other embodiments without departing from the scope of the disclosure. Thus, the disclosure is not intended to be limited to the embodiments shown herein but is to be accorded the widest scope consistent with the principles and novel features disclosed herein.

What is claimed is:
1. An active imaging system for plant growth monitoring comprising:
 (a) an unmanned aerial vehicle equipped with:
  a light emitter capable of emitting light at two or more wavelengths, the light emitter receiving a modula- tion signal from a modulator and emitting light modulated by the modulation signal;

a first lens that projects light from the light emitter onto a crop and a second lens that images an area of the crop onto an array of sensor pixels, a split imaging system such that the area of the crop appears as two images of the same area, at two different wavelengths, on the array of sensor pixels, each pixel of the array of sensor pixels: detecting light reflected by the crop, generating a detection signal, and mixing the detection signal with the modulation signal from the modulator to obtain a reflectivity measurement of the crop; and, (b) a processor that computes a vegetative index based on reflectivity measurements obtained at two or more different wavelengths.

2. The system of claim 1 wherein the split imaging system comprises optical bandpass filters for each of the two wavelengths.

3. The system of claim 1 wherein the unmanned aerial vehicle sends reflectivity measurements to a ground station via a radio link.

4. The system of claim 1, the vegetative index being a normalized difference vegetative index, $$NDVI = \frac{r_{NIR} - r_{VIS}}{r_{NIR} + r_{VIS}},$$

where $r_{NIR}$ and $r_{VIS}$ are crop reflectivity measurements obtained at infrared and visible wavelengths, respectively.

5. The system of claim 1, the second lens being an anamorphic lens.

6. The system of claim 1, the processor comprising logic included in the array of sensor pixels.

7. The system of claim 1, the light emitter comprising a first diode laser that emits light at a visible wavelength and a second diode laser that emits light at an infrared wavelength.

8. A method for plant growth monitoring comprising:
(a) overflying a crop with an unmanned aerial vehicle equipped with:
a light emitter emitting light at two or more wavelengths, the light emitter receiving a modulation signal from a modulator and emitting light modulated by the modulation signal;
a first lens projecting light from the light emitter onto a crop and a second lens imaging an area of the crop onto an array of sensor pixels;
a split imaging system such that the area of the crop appears as two images of the same area, at two different wavelengths, on the array of sensor pixels;
each pixel of the array of sensor pixels: detecting light reflected by the crop, generating a detection signal, and mixing the detection signal with the modulation signal from the modulator to obtain a reflectivity measurement of the crop; and, (b) a processor computing a vegetative index based on reflectivity measurements obtained at two or more different wavelengths.

9. The method of claim 8, the vegetative index being a normalized difference vegetative index, $$NDVI = \frac{r_{NIR} - r_{VIS}}{r_{NIR} + r_{VIS}},$$

where $r_{NIR}$ and $r_{VIS}$ are crop reflectivity measurements obtained at infrared and visible wavelengths, respectively.

10. The method of claim 8, the second lens being an anamorphic lens.

11. The method of claim 10 where the second lens images an area having length and width, and the pixel array obtains alternating visible and infrared reflectivity measurements each time the unmanned aerial vehicle moves by half the length of the imaged area.

12. The method of claim 8, the processor comprising logic included in the array of sensor pixels.

13. The method of claim 8, the array of sensor pixels comprising 10,000 or more pixels.

14. The method of claim 8, the light emitter comprising a first light emitting diode that emits light at a visible wavelength and a second light emitting diode that emits light at an infrared wavelength.

15. The method of claim 8, the light emitter comprising a first diode laser that emits light at a visible wavelength and a second diode laser that emits light at an infrared wavelength.

16. The method of claim 8, the crop comprising a plurality of plants and the second lens imaging an area of the crop onto the array of sensor pixels such that each pixel receives light from more than one plant.

17. The method of claim 8, the crop comprising a plurality of plants and the second lens imaging an area of the crop onto the array of sensor pixels such that each pixel receives light from less than one plant.

18. The method of claim 8, the crop comprising a plurality of plants and the second lens imaging an area of the crop onto the array of sensor pixels such that there is a one-to-one correspondence between plants and pixels.

* * * * *